(12) United States Patent
Mehlmann et al.

(10) Patent No.: US 8,376,573 B2
(45) Date of Patent: Feb. 19, 2013

(54) FLASHLAMP CARTRIDGE FOR REMOVABLE CONNECTION TO A SOCKET

(75) Inventors: Christoph Mehlmann, Diez (DE); Arthur Barlow, Alton (GB)

(73) Assignee: Perkinelmer Technologies GmbH & Co. KG, Wiesbaden (DE)

( * ) Notice: Subject to any disclaimer, the term of this patent is extended or adjusted under 35 U.S.C. 154(b) by 459 days.

(21) Appl. No.: 11/988,529

(22) PCT Filed: Jul. 10, 2006

(86) PCT No.: PCT/IB2006/001908
§ 371 (c)(1),
(2), (4) Date: Nov. 21, 2008

(87) PCT Pub. No.: WO2007/007167
PCT Pub. Date: Jan. 18, 2007

(65) Prior Publication Data
US 2009/0180288 A1    Jul. 16, 2009

Related U.S. Application Data

(60) Provisional application No. 60/698,681, filed on Jul. 13, 2005.

(30) Foreign Application Priority Data
Nov. 9, 2005   (DE) .......................... 10 2005 053 469

(51) Int. Cl.
*F21V 7/20*  (2006.01)
(52) U.S. Cl. ........... 362/218; 362/96; 362/373; 362/294
(58) Field of Classification Search .................. 362/294, 362/218, 373, 96; 439/196
See application file for complete search history.

(56) References Cited

U.S. PATENT DOCUMENTS

| | | | |
|---|---|---|---|
| 2,977,492 A | 3/1961 | Hoekstra | |
| 4,931,912 A * | 6/1990 | Kawakami et al. | 362/547 |
| 5,199,784 A * | 4/1993 | Hempleman | 362/294 |
| 5,493,168 A | 2/1996 | Seedorf | |
| 5,748,837 A * | 5/1998 | Lokar et al. | 392/411 |
| 5,947,592 A * | 9/1999 | Barlow | 362/345 |
| 2002/0145875 A1* | 10/2002 | Roberts et al. | 362/294 |
| 2005/0092469 A1* | 5/2005 | Huang | 165/126 |

FOREIGN PATENT DOCUMENTS

| | | |
|---|---|---|
| EP | 1535582 | 6/2005 |
| JP | 61124900 | 6/1986 |

(Continued)

OTHER PUBLICATIONS

European Office Action, EP Application No. 06 795 096.4, dated Apr. 14, 2011, 4 pages.

(Continued)

*Primary Examiner* — Julie Shallenberger
(74) *Attorney, Agent, or Firm* — MH2 Technology Law Group, LLP

(57) ABSTRACT

A flashlamp cartridge (10) comprises an cartridge portion for a flashlamp (1), cooling device components for a cooling device (11, 12) for the flashlamp, one or more thermal cartridge terminals (13) for the cooling device for thermally connecting the flashlamp cartridge to a socket, and one or more electrical cartridge terminals (14) for the flashlamp for electrically connecting the flashlamp cartridge to a socket. A flashlamp assembly comprises such flashlamp cartridge (10) and a flashlamp (1) accommodated in the flashlamp cartridge. A socket for a flashlamp assembly comprises corresponding electric socket terminals (24) and thermal socket terminals (23). An electrical device comprises such socket.

13 Claims, 4 Drawing Sheets

FOREIGN PATENT DOCUMENTS

| | | |
|---|---|---|
| JP | H01170207 | 12/1989 |
| JP | 200318 | 1/1990 |
| JP | 4325139 | 11/1992 |
| JP | 8313340 | 11/1996 |
| JP | 2004524927 | 8/2004 |
| JP | 2005509485 | 4/2005 |
| WO | 02/082866 | 10/2002 |
| WO | 02082866 | 10/2002 |
| WO | 03043514 | 5/2003 |
| WO | 2004/096072 A1 | 11/2004 |
| WO | 2004096072 | 11/2004 |

OTHER PUBLICATIONS

German Patent Office, German Patent Application No. 10 2005 053 469.4-54, Office Action dated Apr. 30, 2009, 3 Pages.

Notice of Reasons for Rejection (English translation) dated Nov. 29, 2011, Japanese Patent Application No. 2008-520976, 10 pgs.

* cited by examiner

FLASHLAMP CARTRIDGE FOR REMOVABLE CONNECTION TO A SOCKET

This application claims priority to U.S. Provisional Application Serial No. 60/698,681 filed Jul. 13, 2005, the disclosure of which is incorporated herein by reference

BACKGROUND OF THE INVENTION

The invention relates to a flashlamp cartridge, a flashlamp assembly, a socket and an electrical apparatus.

BACKGROUND

Flashlamps are increasingly used for cosmetic and medical/therapeutic purposes. In doing so, flashlamps generate preferably periodic flashes which are radiated e.g., on the skin to treat skin areas. On the one hand, flashlamps generate the desired radiation energy in the form of visible and invisible (UV, IR) light, but on the other hand they also generate undesired heat and therefore need to be cooled. Therefore, in previous devices a structure has been provided which ensures the electrical supply on the one hand and the thermal supply on the other hand for the flashlamp. Usually, the flashlamps are cooled by liquid. If such a flashlamp needs to be replaced, this leads to a laborious process of removing the thermal connections, wherein, if necessary, it must be insured that no cooling liquid leaks in an undesired manner, and of removing the electrical connections. Then the flashlamp can be exchanged. Subsequently, the cooling circuit must be refilled with water and reconnected and the electrical connections must be made. Ultimately, this process is so laborious that it must be performed by trained service staff and cannot be carried out by the user of the apparatus. Therefore, the replacement of the flashlamp is tedious and expensive. In addition to this, if a new flashlamp is exchanged for an old flashlamp, the wrong flashlamp type may be used.

EP 0724894 describes an apparatus for therapeutic electromagnetic treatment. A light source is disposed within an enclosure including a reflector. The radiated light is collected by a light guide and transmitted to the treatment region.

U.S. Pat. No. 5,830,208 describes an apparatus for treating dermatological conditions with radiation. A flashlamp is mounted in the focal point of a reflector within a casing. A Peltier cooling device is provided for the treatment area of the patient's skin.

U.S. Pat. No. 4,644,550 describes a liquid-cooled laser. It comprises a resonator of small size having a fluid cooled laser body which may be dissembled without detuning the resonator, a closed cooling circuit, a supply unit of small size and an electronic circuit.

WO 01/62170 describes an apparatus and a method for the heat-treatment of the skin. It comprises means for generation of electromagnetic radiation, means for concentration of said radiation, means for conversion of said electromagnetic radiation energy into heat in a thin absorbing layer, means for effective cooling of redundant heat generated in the absorbing layer and pre-cooling of dermal layers, and means for effective thermal conduction between the absorptive layer and the object surface to be heated. The means for generating electromagnetic radiation may be an electric lamp with a pulse length of 500 ms maximum. It may be a gas-discharge arc lamp.

It is the object of the invention to provide a flashlamp cartridge, a flashlamp assembly, a socket and an electrical apparatus which allow the simple exchange of flashlamps.

This object is achieved by means of the features of the independent claims. The dependent claims are directed to preferred embodiments of the invention.

A flashlamp cartridge according to the invention includes a region for the flashlamp, cooling device components for a cooling device for the flashlamp, thermal terminals at the cartridge for the cooling device to be able to thermally connect the cartridge with a socket, and one or more electrical terminals at the cartridge to electrically connect the flashlamp cartridge to the socket.

Such a flashlamp cartridge may be prefabricated separately from the flashlamp. After it has been fabricated or pre-fabricated, the flashlamp may be inserted to form a flashlamp assembly together with the flashlamp cartridge. This flashlamp assembly may be handled as a unit and in particular it may be connected as a unit with a corresponding socket having appropriate socket terminals for thermal and electrical connection. The thermal as well as the electrical terminals of the cartridge may comprise connectors fixedly provided on the flashlamp cartridge. They may be plug-type connectors having the same plug-in direction. The flash lamp cartridge may form an enclosure which partially or completely surrounds the flash lamp. A duct for cooling the flash lamp by means of a fluid may be provided in such enclosure. The fluid may flow around the flash lamp.

A socket is formed complementary to the flashlamp assembly insofar as this is necessary for the thermal and electrical and possibly also the mechanical connection. The socket comprises electrical and thermal socket terminals for the flashlamp assembly. The socket is a part of an electrical device which may e.g., be a cosmetic device or a medical/therapeutic device. The device may be an IPL ("intense pulsed light") application. It may be a device for drying, sterilizing or curing. The socket may be fixedly connected to the device or it may be connected to the device via a flexible line or a loom of cables which on the one hand make it possible to supply and remove the cooling fluid and on the other hand enable the electric supply.

When the flashlamp is exchanged the flashlamp assembly may be pulled off and replaced by an available one. The pulled-off assembly may be discarded or recycled.

Next, single embodiments of the invention will be described with reference to the drawings, wherein:

DETAILED DESCRIPTION

Figure 1:
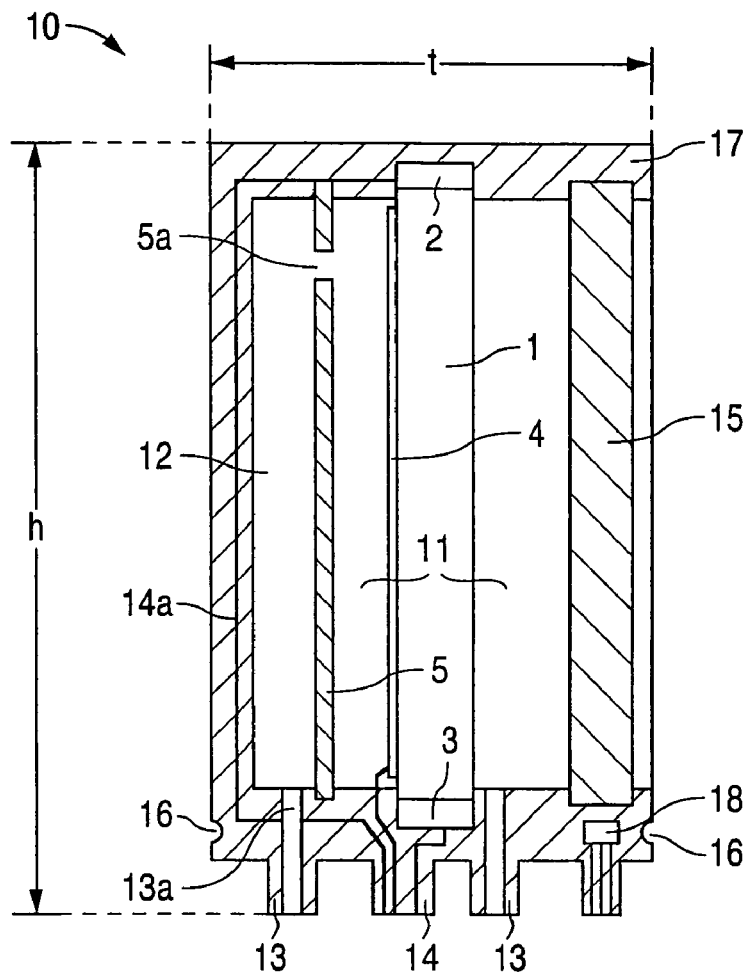
FIG. 1 shows a schematic longitudinal section of a flashlamp assembly and a corresponding socket.
Figure 1:
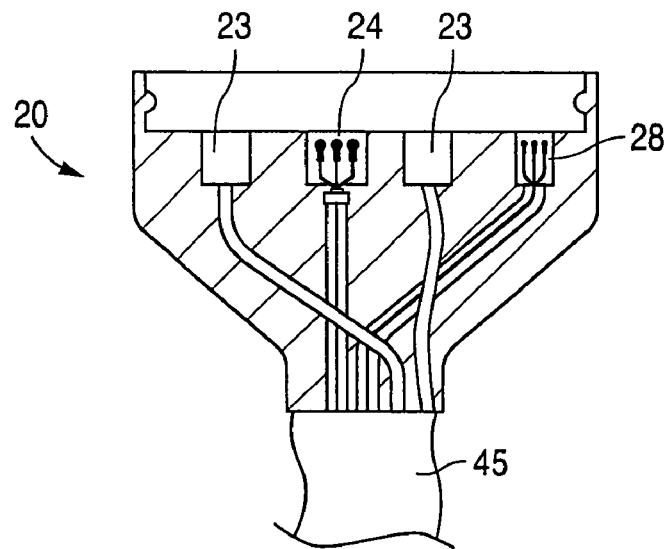

The top half of FIG. 1 schematically shows a longitudinal section of a flashlamp assembly 10 and at the bottom half shows a corresponding socket 20, also as a section. The flashlamp assembly includes a flashlamp 1 and a flashlamp cartridge or body (reference numerals 5, 11-18). The flashlamp cartridge may be manufactured and sold separately from the flashlamp. At a later manufacturing step the flash lamp 1 may be inserted into the flashlamp cartridge in order to produce what is defined in this description as the flashlamp assembly 10 (as shown as a section in FIG. 1).

The flashlamp 1 can radiate incoherent light. It may include electrical contacts 2 and 3 as well as an ignition electrode 4 which may be formed, for example, as an electrode along the outside of the glass tube of the flashlamp. However, the ignition electrode 4 may also be manufactured separately from the flashlamp 1, e.g., as a structural member of the flashlamp cartridge. The flashlamp can also radiate coherent light. Then it may be a pulsed laser.

The flashlamp cartridge comprises at least components of a cooling device. The cooling device can be a duct at least partly set up for a cooling fluid. In FIG. 1 reference numeral 11 denotes an outlet duct and reference numeral 12 denotes an inlet duct. In this embodiment, a reflector 5 forms the partition wall between the outlet duct 11 and the inlet duct 12 which may in fluid communication via a small opening 5a in the reflector. Depending on the construction type, the flashlamp cartridge may already form a complete cooling duct. Optionally, however, it may also be constructed such that it becomes complete and in particular fluid-tight only after the flashlamp and possibly further components have been inserted. The cooling ducts are a part of a cooling device 11, 12 which also comprises one or more thermal cartridge terminals 13 for supplying and/or removing a cooling fluid, such as water or air. In the case of air cooling a single terminal 13 may optionally be provided. For heated discharge air or supply air an outlet or inlet opening, respectively, (not shown) may be provided.

The flashlamp cartridge and the flashlamp assembly 10, respectively, also include one or more electrical cartridge terminals 14 for the flashlamp 1. They may be terminals for electrical energy and/or control signals. For example, the control signals may be ignition pulses for the ignition electrode 4 of the flashlamp. However, the cartridge may also comprise an electric or electronic circuit (not shown) which suitably generates signals for the flashlamp 1 in a more or less complex formation. The flashlamp 1 and its drive circuit, respectively, will be supplied with energy and/or control signals via the electrical cartridge terminals.

A transparent area 15, for example an optical window, enables the radiation energy generated by the flash lamp 1 to exit the cartridge. The optical window 15 may also have filtering and/or polarization and/or focussing characteristics. Generally, the optical window 15 may be a transparent material 15 in a flat or tabular shape. It may be glass, hard glass, quartz glass or plastics, acrylic glass or the like. It may be a separate constructional member which is inserted into a corresponding opening and supported therein. The optical window 15 may also include the beginning of a waveguide 31 (FIG. 3) or it may be such a beginning that the radiation energy may be guided away from the flashlamp 1 by the waveguide. The waveguide may be a flexible or a rigid waveguide. Preferably, the optical window 15 is located opposite the reflector 5. The optical window may be cooled by the cooling fluid at least from one side. It may form a part of the wall of the cooling duct.

The flashlamp 1 is at least partly surrounded by the cooling fluid moving in the duct 11, 12. FIG. 1 shows an embodiment wherein the electrical contacts 2, 3 are not immersed in the cooling fluid. However, the electrical contacts may also be immersed in the cooling duct 11, 12. Then it will have to be ensured that the cooling fluid is not conductive. For example, deionized water or a suitable gas may then be used.

A reflector 5 may be provided for guiding the beam of the light emitted by the flashlamp 1. It may be a parabolic reflector, an elliptical reflector or any other suitable reflector shape. As suggested in FIG. 1, the reflector may be a separate constructural member which is suitably supported in the flashlamp cartridge, for example by being cast in an injection-molded part or positioned by appropriate holding and guiding portions. The reflector may lie in the cooling duct and surrounded by cooling fluid. In the embodiment shown in FIG. 1 the reflector may form the partition wall between optionally provided inlet and outlet ducts.

The flashlamp cartridge comprises an enclosure 17 in and on which the described components are formed, mounted, received and enclosed, respectively. The enclosure 17 may be assembled from several single parts, for example from two parts, which, however, is not shown in FIG. 1. These parts and generally the basic body of the enclosure 17, respectively, may be or include a plastics injection molding.

A mechanical connection means 16 apart from the electrical and thermal connection also effects the mechanical connection, support and orientation of the flashlamp assembly with respect to the socket or baseplate 20. The orientation may be effected by a specific form closure. The support may be effected by snap-on means or the like.

If necessary, the flashlamp assembly 10 includes electric lines 14a which connect the electrodes 2, 3, 4 of the flashlamp 1 and optionally further electric and electronic components with each other and the electrical cartridge terminals 14. If required, the flashlamp assembly 10 also includes one or more fluid conduits 13a which connect the cooling duct 11, 12 to the thermal cartridge terminals 13.

During pulsed operation the flashlamp may have an average radiation power of >20 W, preferably >50 W, <1,000 W, preferably <500 W. The flashlamp may be straight or bent in a U shape or a helical shape.

Reference numeral 20 denotes a socket which as to its function is formed to complementary match the connections of the flashlamp cartridge. Socket 20 includes terminals 23 and 24 corresponding to the cartridge terminals 13 and 14 at the flashlamp cartridge. The socket comprises one or more thermal socket terminals 23 and one or more electric socket terminals 24 for energy and/or control signals for the flashlamp.

The terminals for electricity and/or thermal at the flashlamp cartridge and/or at the socket may be or include plug type connectors. They may be oriented towards the same plug-in directions.

The socket may have positive fit with a portion of the flashlamp cartridge to effect the orientation of the flashlamp cartridge with respect to the socket. The positive fit may be effected by arranging the terminals 13, 14, 23 and 24 at the flashlamp cartridge and the socket.

The flashlamp cartridge can include a first identification means 18 by virtue of which it is possible to identify characteristic values of the flashlamp cartridge and/or of the flashlamp. For example, the type of flashlamp cartridge or the type of flashlamp can be identified by way of the identification means 18. The identification means may be designed to be mechanical in that the flashlamp cartridge may require a specific socket-side positive fit in the area of the terminals which only a matching socket 20 will provide. However, the identification means 18 may also be an electronic identification, for example by way of a chip embedded in the flashlamp cartridge, which transmits particular, optionally encoded data written in before via a connection and particularly an electrical plug type connection 18, 28, or keeps them such that they can be read out so that the device may decide whether a flashlamp cartridge or a flashlamp, respectively, having the correct characteristic data has been inserted. If so, operation may begin. If not, operation will be prevented or a warning or the like will be issued. Instead of a chip, an electronic circuit may generally be provided. The chip or circuit may be enclosed and separately usable and include two electrical terminals.

Figure 2:
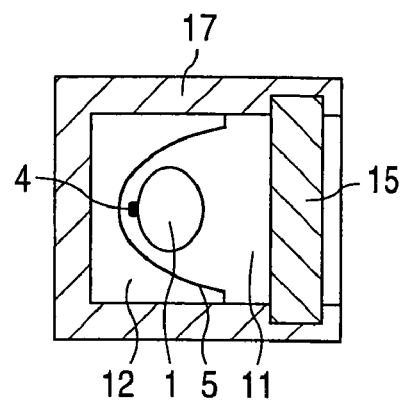
FIG. 2 shows a schematic cross section of the flashlamp assembly.

The letter h in FIG. 1 is a symbol for the height and the total length, respectively, of the flashlamp assembly. It may be >5 cm, preferably >10 cm. It may be <50 cm, preferably <20 cm. The letter t symbolizes the depth of the flashlamp cartridge (measured in the radiation direction). It may be >0.5 cm. It may be <6 cm, preferably <4 cm. The width b of the flash lamp cartridge (perpendicular to the height and depth as shown in FIG. 2) may be >1 cm. It may be <6 cm, preferably <4 cm.

Figure 3:
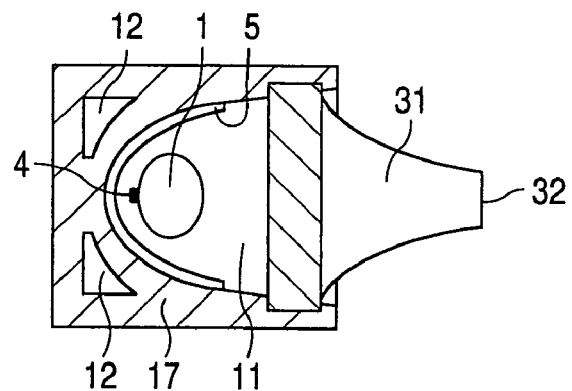
FIG. 3 shows a schematic cross section of another embodiment of the flashlamp assembly.

FIGS. 2 and 3 show cross-sections of the flashlamp cartridge and the flashlamp assembly 10, respectively. The same reference numerals as in FIG. 1 denote the same components. In FIG. 2 the reflector 5 forms the partition wall between the cooling fluid flowing out and the cooling fluid flowing back, i.e., between the ducts 11 and 12. It may be suitably fixed on or in the wall of the enclosure 17. In the embodiment of FIG. 3 the fluid inlet is formed by one or more ducts 12 leading back through walls of the enclosure which are appropriately fluidly connected to duct 11. In the embodiment as shown the reflector 5 is not constituted by a separate constructional member but by a suitable coating of the wall of the enclosure 17. Again, it should be noted that the enclosure 17 may be composed of several constructional members. In the embodiments of FIGS. 2 and 3 the flashlamp 1 is surrounded by the cooling fluid in the duct 11 and thus cooled. The fluid may be water or gas, for example air. The cooling fluid may also surround the electrical contacts of the flashlamp. If necessary, deionized or distilled water is to be used to reduce losses.

In FIG. 3, 31 symbolizes a waveguide which passes on the light from the flashlamp and guides it to the radiation surface 32. Thus, a clearly defined radiation surface can be created. The waveguide 31 may be rigid or flexible. It may be integrally formed with the transparent material 15 of the window or attached thereon, as indicated in FIG. 3. The waveguide is placed on top of the window and delivers light to the other side of the waveguide which is in contact with the patient's skin. In this manner, the waveguide provides a controlled light fluence to the skin, as well as isolating the high voltages, etc., on the lamp from the patient. The entire waveguide may be formed as a component of the cartridge—fixed to the housing—possibly even performing the window and coolant seal job as well. Alternatively, a first portion of the waveguide can be formed on the cartridge (and hence removable when the cartridge is changed) and a second portion of the waveguide can be part of the treatment unit. The two portions would be aligned when the cartridge was installed.

The flashlamp cartridge may include an optical filter and/or a light diffuser and/or a focussing means, in particular a Fresnel lens and/or a polarizer.

Figure 4:
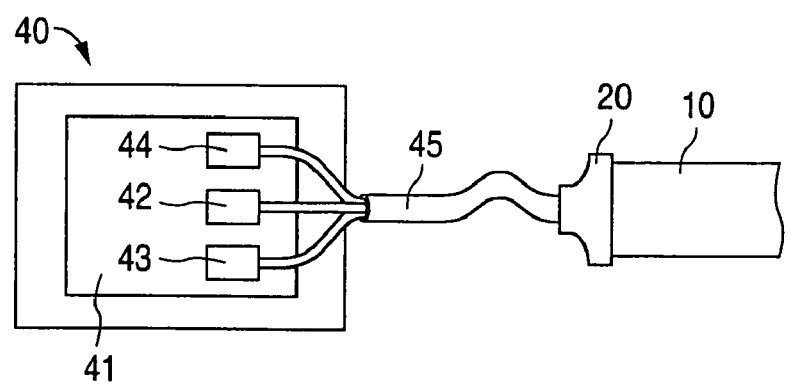
FIG. 4 shows the overall electric device including the socket and the flashlamp assembly.

FIG. 4 schematically shows the overall assembly of a device 40. It comprises the basic device 41 for the primary functions of the device and for the flashlamp includes an electric source/drive 42, a thermal cooling module 44 and optionally an authentication module 43 for the authentication device 18, 28 of FIG. 1. Furthermore, the device comprises a socket 20 connected to the basic device 41. The socket 20 may be rigidly connected to the basic device 41 of the electric device 40 or connected thereto via a flexible connection 45. The flashlamp assembly 10 is plugged into the socket 20. Thus, it can be easily removed and inserted.

In the device 40 a monitoring means (not shown) may be provided which monitors the flashlamp, for example by measuring the operation time or counting the light pulses. These may be compared to predetermined values which e.g., may result from the authentication means 18. If the result shows that a particular operation time has been reached, a warning may be issued. The monitoring means may be provided in the basic device 41 or in the socket 20 or in the flashlamp assembly 10.

The authentication means 18 can be in the form of validation hardware that allows the system manufacturer to control the use of the lamp, in order to substantially prevent misuse. The validation hardware can carry information relevant to the lamp within that specific cartridge. Relevant information can include, for example, the rated life, maximum permissible number of flashes, serial numbers, and/or a on-going counter for actual flashes used thus far. The hardware 18 can be integrated within the cartridge, such that the information follows the lamp wherever the lamp is used (somewhat similar to a "dongle" or security ID). For example, the maximum number of light flashes can be limited to prevent explosions and/or degrading of any filters. The lamp assembly also can provide the ability to lock out non-approved lamps, in order to prevent explosions, emission along an erroneous spectral range, and/or incorrect pulse energy. An assembly also can provide an electrical safety interlock to discharge/de-energize any electrical connectors allowing the cartridge to be safely detached from the base plate. The interlock also can prevent detachment without first discharging the assembly.

In one example, the validation hardware connections (and any cover) can be arranged to break an electrical connection before connections for the main lamp and fluid system are opened. The validation hardware connections typically will be at a relatively safe lower voltage, while the main lamp connections carry a much higher voltage. A validation connection break and/or cover removal switch can be used as a signal to shut down the parent system, thereby providing no fluid flow and zero voltage on the lamp connections. In addition, the high-voltage connectors themselves can be designed to prevent human contact by controlling parameters such as the shape and dimensions of the connectors, in accordance with relevant electrical safety practice.

Figure 5:
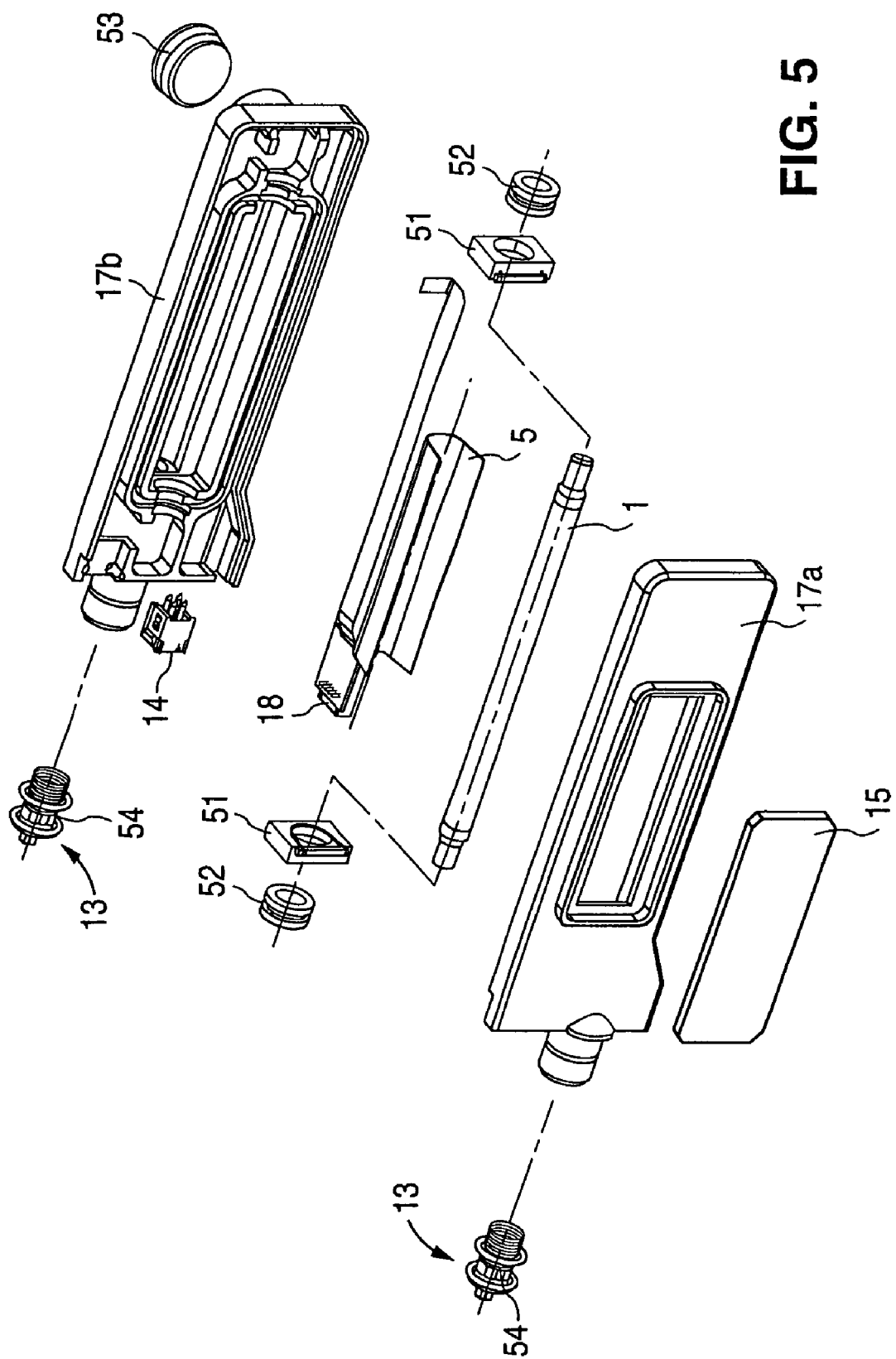
FIG. 5 shows an exploded view of the flashlamp assembly.

FIG. 5 shows a possible construction of a flashlamp cartridge in an exploded drawing. 17a and 17b are halves of an enclosure or body 17 which may substantially form the flashlamp cartridge. 1 is the flashlamp itself. The parts 17a and 17b may be assembled—optionally with sealing means which can include rubber bands or more preferably glue so that they form a permanent, leak tight, sealed enclosure in which the flow ducts for the cooling fluid are formed after the assembly. Suitable snap-on means may be provided. The reflector 5 is formed by a separate constructional member which is put into the provided cartridge. 51 are holding and orientation elements for the reflector in relation to the flashlamp, which in turn may be positioned and supported in the parts 17a and 17b. These elements comprise an opening for the flashlamp ends such that they are able to position the reflector in relation to the flashlamp. 52 are sealing rings for sealing the fluid duct. 53 symbolizes an operating element which may be provided at the flashlamp cartridge. For example, it may be an electric switch which enables or prevents the supply of electrical pulses to the flashlamp. Furthermore, display elements and sealing devices (not shown) may be provided.

54 symbolizes a valve means for the cooling fluid which may for example be provided in a thermal cartridge terminal 13. The valve may be formed such that it automatically opens when the flashlamp cartridge is plugged into the allocated socket and thus releases the flow duct, whereas it automatically closes when the flashlamp cartridge is pulled out of the socket, thus shutting the cooling duct and thus preventing the cooling fluid from leaking. Instead of an automatic operation during the plug-in process a manual operation may be provided. Such a valve 54 may be provided at both thermal cartridge terminals 13. Such a valve may be provided at the socket side thermal terminals 23. Then it will be ensured that no cooling fluid leaks from the device side cooling circuit either.

The flashlamp cartridge may comprise an explosion protective means (not shown) which protects the environment against a possibly exploding flashlamp. The explosion protective means may include separate, particularly stable retention members and/or may be formed by a particularly stable design of the components which need to be provided anyway. Especially the enclosure 17 and/or the transparent portion 15 as well as their connection may be designed more stable than their normal mechanical stress would require.

The flashlamp cartridge may include another outer enclosure (not shown) which surrounds the inner enclosure 17. The electrical and thermal cartridge terminals may be provided on the outer surface of the outer enclosure or on the outer surface of the inner enclosure.

Figure 6A:
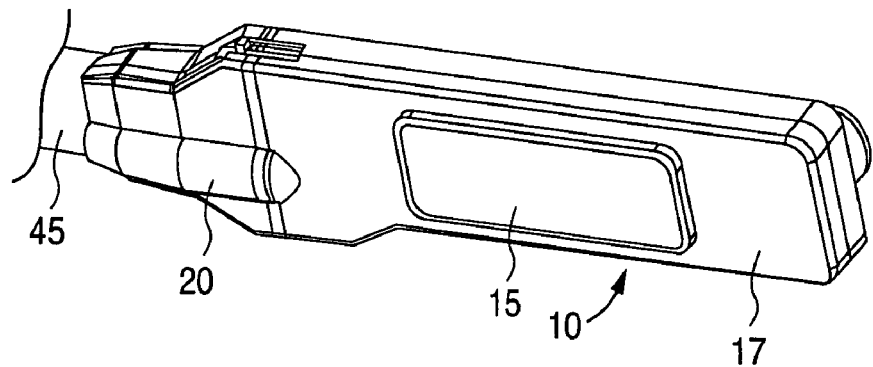
FIGS. 6a and 6b show the socket and the flashlamp assembly in an assembled and a dissembled state.
Figure 6B:
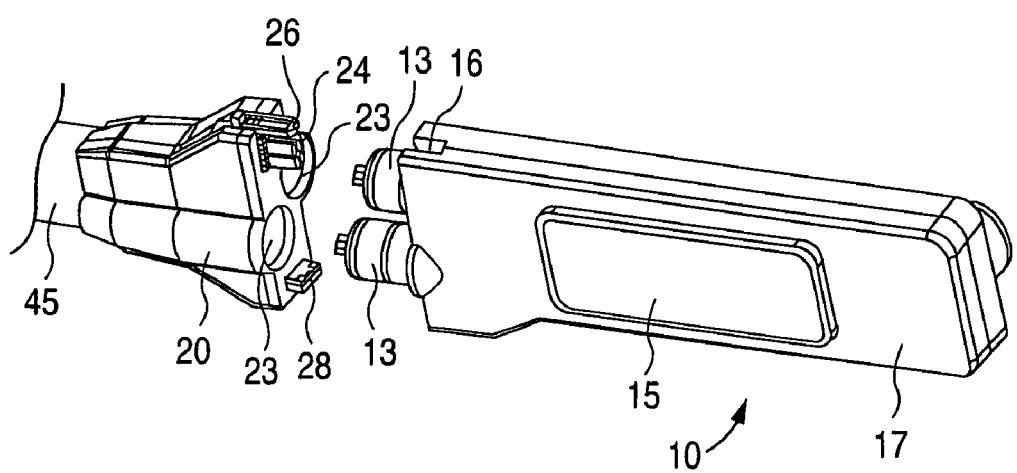

FIG. 6a shows the flashlamp assembly 10 as connected to the socket 20. To the left there are electrical connections and the cooling fluid conduits. They may be combined to form a uniform supply train 45. FIG. 6b shows the flashlamp assembly 10 when it is removed from the socket 20. Then it becomes possible to see the respective electrical and thermal terminals 13, 14, 23 and 24. The terminal 28 for the authentication means can be seen, too. 26 symbolizes a locking element which co-operates with a corresponding portion 16 in the flashlamp assembly.

The flashlamp assembly 10 may be formed as a cartridge completely enclosing the flashlamp. It may be prefilled with cooling fluid and sold that way. The cooling fluid may have filter characteristics, for example, by mixing water with specific absorption agents.

FIGS. 1, 5 and 6 show embodiments wherein all terminals 13, 14 are provided on one side (face surface) of the flashlamp assembly. In other embodiments (not shown) the terminals may also be located on two preferably opposite sides. They may be provided in their plug-in direction perpendicular to the longitudinal direction of the assembly 10 and of the flashlamp 1, respectively.

What is claimed is:

1. A cartridge for an intense pulsed light device, said cartridge comprising:
    a flashlamp held within the cartridge and configured to generate pulses of light;
    a window positioned to be aligned with the flashlamp;
    a reflector configured to reflect light from the flashlamp, the reflector being positioned within the cartridge and aligned with the flashlamp on the side opposite the window;
    a cooling duct formed in the cartridge and in thermal communication with the flashlamp;
    at least two thermal connectors to provide fluid communication line between a socket of the intensed pulse light device and the cooling duct in the cartridge; and
    an electrical connector to provide an electrical connection between the socket and the flashlamp, wherein the at least two thermal connectors and the electrical connector are of a plug type located on a same side of the cartridge, and wherein the at least two thermal connectors and the electrical connector have the same plug-in direction,
    wherein said cartridge is configured to be removably connected to a socket of the intense pulsed light device, the at least two thermal connectors and the electrical connector being configured to be inserted into the socket in unison with one another.

2. The cartridge as recited in claim 1, wherein the window forms a portion of a wall of the cooling duct.

3. The cartridge as recited in claim 1, wherein the reflector forms a portion of a wall of the cooling duct.

4. The cartridge as recited in claim 1, wherein the at least two thermal connectors comprise a first connector that defines a fluid inlet to the cooling duct and a second connector that provides a fluid outlet from the cooling duct to the socket.

5. The cartridge as recited in claim 1, wherein said at least two thermal connectors includes a valve configured to selectively permit fluid flow through the at least one of the at least two thermal connectors based on a connection state of the cartridge.

6. The cartridge as recited in claim 1, further including an identification device enabling detection of a characteristic of the cartridge and/or the flashlamp.

7. The cartridge as recited in claim 6, wherein the identification device provides information about the characteristic of the cartridge to the socket.

8. The cartridge as recited in claim 6, wherein the identification device is mechanical and/or electronic.

9. A flashlamp assembly adapted to be connected to a socket of an intense pulsed light device, comprising:
    a flashlamp configured to generate pulses of light;
    a cartridge for holding the flashlamp and including a cooling duct;
    an electrical connector providing an electrical connection to the flashlamp, said electrical connector including a quick release connector for interfacing with the socket;
    at least two thermal connectors configured to pass a fluid about the flashlamp, said at least two thermal connectors including a quick release connector configured to interface with the socket, said at least two thermal connectors being physically separated from the electrical connector, and providing fluid to the cooling duct; and
    a reflector positioned within the cartridge and forming a portion of the cooling duct, the reflector being configured to reflect light from the flashlamp.

10. The flashlamp assembly as recited in claim 9, further including validation hardware for carrying information about the flashlamp and which is operable to generate a signal that can control the operation of the flashlamp.

11. The flashlamp assembly as recited in claim 10, wherein said validation hardware operates at a lower voltage than the flashlamp voltage.

12. The cartridge of claim 6, wherein the characteristic includes at least one of a type associated with the flashlamp, a type associated with the cartridge, an identity associated with the flashlamp, and an identity associated with the cartridge.

13. A cartridge for an intense pulsed light device, said cartridge comprising:
    a rectilinear flashlamp held within the cartridge and configured to generate pulses of light;
    a window positioned to be aligned with the flashlamp;
    an elongated concave reflector configured to reflect light from the flashlamp through the window, the reflector extending over a major portion of the length of the rectilinear flashlamp, and being positioned within the cartridge and aligned with the flashlamp on the side opposite the window;
a cooling duct formed in the cartridge and in thermal communication with the flashlamp;
at least two thermal connectors to provide fluid communication between the socket and the cooling duct in the cartridge; and
an electrical connector to provide an electrical connection between the socket and the flashlamp, wherein the at least two thermal connectors and the electrical connector are of a plug type located on a same side of the cartridge, and wherein the at least two thermal connectors and the electrical connector have the same plug-in direction,
wherein said cartridge is configured to be removably connected to a socket of the intense pulsed light device.

* * * * *